United States Patent
Wang et al.

(10) Patent No.: US 10,446,758 B2
(45) Date of Patent: Oct. 15, 2019

(54) HOLE TRANSPORTING MATERIAL, OLED DISPLAY PANEL AND ELECTRONIC DEVICE COMPRISING THE SAME

(71) Applicants: SHANGHAI TIANMA AM-OLED CO., LTD., Shanghai (CN); TIANMA MICRO-ELECTRONICS CO., LTD., Shenzhen (CN)

(72) Inventors: Xiangcheng Wang, Shanghai (CN); Wei He, Shanghai (CN); Ying Liu, Shanghai (CN); Jinghua Niu, Shanghai (CN); Yuji Hamada, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 205 days.

(21) Appl. No.: 15/640,582

(22) Filed: Jul. 3, 2017

(65) Prior Publication Data
US 2017/0301864 A1  Oct. 19, 2017

(30) Foreign Application Priority Data
Dec. 28, 2016 (CN) .......................... 2016 1 1237792

(51) Int. Cl.
*H01L 51/00* (2006.01)
*C07C 211/54* (2006.01)
(Continued)

(52) U.S. Cl.
CPC ........ *H01L 51/0059* (2013.01); *C07C 211/54* (2013.01); *H01L 51/005* (2013.01); *H01L 51/002* (2013.01); *H01L 51/0058* (2013.01); *H01L 51/0072* (2013.01); *H01L 51/0077* (2013.01); *H01L 51/0085* (2013.01); *H01L 51/5036* (2013.01); *H01L 51/5056* (2013.01); (Continued)

(58) Field of Classification Search
CPC ...................................................... C07C 211/54
See application file for complete search history.

(56) References Cited

U.S. PATENT DOCUMENTS

| | | | | |
|---|---|---|---|---|
| 5,550,290 A | | 8/1996 | Mizuta et al. | |
| 5,629,117 A | * | 5/1997 | Katsukawa | G03G 5/0564 430/83 |
| 5,639,914 A | * | 6/1997 | Tomiyama | C07C 211/54 552/110 |

FOREIGN PATENT DOCUMENTS

| CN | 102148334 A | 8/2011 |
|---|---|---|
| JP | 8220788 A | 8/1996 |

(Continued)

OTHER PUBLICATIONS

English machine translation of Ueda et al., JP 2004-047442 (Year: 2004).*

*Primary Examiner* — Peter F Godenschwager
(74) *Attorney, Agent, or Firm* — Kilpatrick Townsend & Stockton LLP

(57) ABSTRACT

The present invention relates to a hole transporting material having a structure of formula (I). (1) The present invention provides a hole transporting material having at least one benzene ring with non-hydrogen substituent(s) in the formula and being capable of obtaining a suitable mobility rate without occurrence of crosstalk between pixels. (2) The hole transporting material provided by the present invention is capable of satisfying the requirements on MASK cleaning in terms of solubility (NMP solvent).

16 Claims, 2 Drawing Sheets

(51) Int. Cl.
 *H01L 51/50* (2006.01)
 *H01L 51/52* (2006.01)
(52) U.S. Cl.
 CPC ...... *H01L 51/5072* (2013.01); *H01L 51/5088* (2013.01); *H01L 51/5092* (2013.01); *H01L 51/5206* (2013.01); *H01L 51/5221* (2013.01); *H01L 2251/5376* (2013.01); *H01L 2251/558* (2013.01)

(56) References Cited

FOREIGN PATENT DOCUMENTS

| | | | |
|---|---|---|---|
| JP | 2003313547 A | 11/2003 | |
| JP | 2004047442 A | 2/2004 | |

* cited by examiner

HOLE TRANSPORTING MATERIAL, OLED DISPLAY PANEL AND ELECTRONIC DEVICE COMPRISING THE SAME

CROSS-REFERENCE TO RELATED APPLICATIONS

The application claims the benefit of the earlier filing date of C.N. Patent Application No. 201611237792.X, filed on Dec. 28, 2016, the contents of which are incorporated by reference herein in its entirety.

TECHNICAL FIELD

The present invention relates to the field of preparation of organic light-emitting diodes, and more particularly to a hole transporting material, an OLED display panel and an electronic device comprising the same.

BACKGROUND

Mobile phones and many other small and medium size OLED screens use R, G, B sub-pixel display mode (FIG. 1). In order to improve the production yield, some functional layers are often designed as public layers, so that FMM (fine metal mask) can be used less. Hole transporting layer often uses a public layer, and general public hole transporting layer may use commercially available materials. The commercially available hole transporting layer materials have a molecular structure of, e.g.

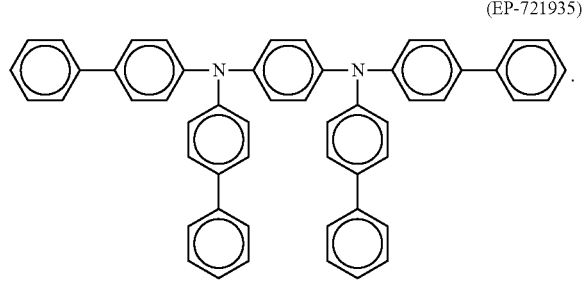

(EP-721935)

However, such material has a higher longitudinal mobility rate, and the lateral mobility rate thereof is not very high. There will be no occurrence of crosstalk between pixels.
CN103108859 discloses

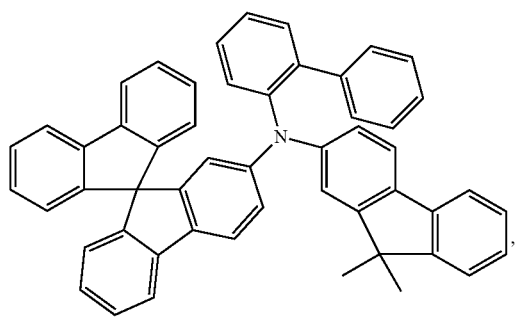 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

wherein the material has a good solubility, and a higher mobility rate.

There are several problems in the current technologies of hole transporting materials. First, the material solubility is not good, which will lead to a worse cleaning effect of Mask for evaporation during mass production. Second, the material mobility rate is too low, which will lead to an excessive overall voltage of devices. Third, the mobility rate of the material, especially the lateral mobility rate of the material, is too high, leading to crosstalk of adjacent pixels.

The mobility rate of the commercially available material in EP-721935 falls within the acceptable range, and no crosstalk will occur. However, the solubility thereof is not very good. The solubility of the commercially available material in CN103108859 is acceptable, but too high mobility rate leads to lateral leakage current to form crosstalk.

Accordingly, there is a need in the art to develop a hole transporting material having a suitable mobility rate without occurrence of crosstalk between adjacent pixels.

SUMMARY

In view of the deficiencies of the prior art, the present invention provides, on one aspect, a hole transporting material having a structure of formula (I):

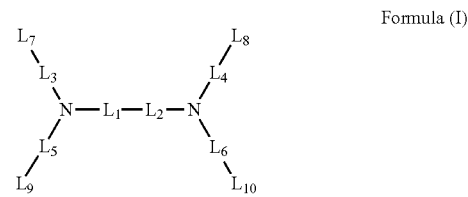

Formula (I)

wherein $L_1$, $L_2$, $L_3$, $L_4$, $L_5$ and $L_6$ are each independently anyone selected from the group consisting of unsubstituted phenylene and phenylene containing substituent(s);
$L_7$, $L_8$, $L_9$ and $L_{10}$ are each independently anyone selected from the group consisting of unsubstituted phenyl and phenyl containing substituent(s);
at least one of $L_1$ and $L_2$ is phenylene containing substituent(s);
$L_3$, $L_4$, $L_5$, $L_6$, $L_7$, $L_8$, $L_9$ and $L_{10}$ are required to satisfy at least one of the following conditions:
(1) at least one of $L_3$, $L_4$, $L_5$ and $L_6$ is phenylene containing substituent(s);
(2) at least one of $L_7$, $L_8$, $L_9$ and $L_{10}$ is phenyl containing substituent(s).

On another aspect, the present invention provides a hole transporting layer comprising the hole transporting material as stated above.

On yet another aspect, the present invention provides an OLED display panel comprising a first electrode and a second electrode, wherein a laminate comprising a light emitting layer and a hole transporting layer is provided between the first electrode and the second electrode; the hole transporting layer comprises the hole transporting material as stated above, or the hole transporting layer is the hole transporting layer as stated above.

On still another aspect, the present invention provides an electronic device comprising the OLED display panel as stated above.

As compared to the prior art, the present invention has the following beneficial effects:

(1) The present invention provides a hole transporting material having at least one benzene ring with non-hydrogen substituent(s) in the formula and being capable of obtaining a suitable mobility rate without occurrence of crosstalk between pixels.

(2) The hole transporting material provided by the present invention is capable of satisfying the requirements on MASK cleaning solvent in terms of solubility (NMP solvent). The MASK cleaning solvent is anyone selected from the group consisting of ketones, furans or alcohols, or a combination of at least two selected therefrom. Cyclohexanone (HC), N-methylpyrrolidone (NMP), substituted or unsubstituted furan, isopropyl alcohol and the like are more commonly used.

DETAIL DESCRIPTION

Figure 1:
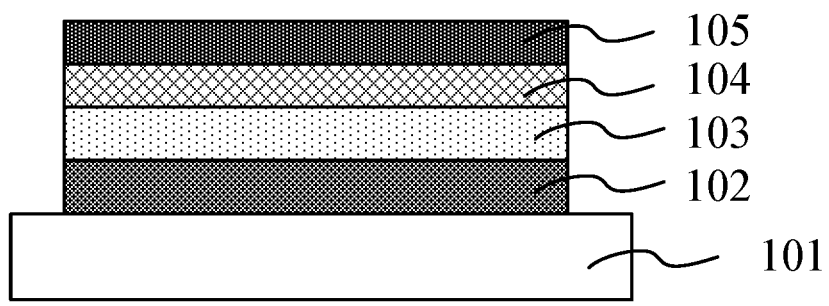
FIG. 1 shows a schematic cross-sectional structure view of an OLED display panel according to one specific embodiment of the present invention.

For the purpose of understanding the present invention, the present invention discloses the following examples. Those skilled in the art shall know that the examples are merely illustrative of the present invention and should not be construed as limiting the present invention.

In one specific embodiment, the present invention provides a hole transporting material having a structure of formula (I),

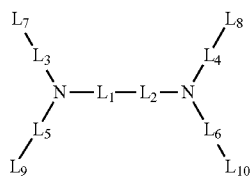

Formula (I)

wherein $L_1$, $L_2$, $L_3$, $L_4$, $L_5$ and $L_6$ are each independently anyone selected from the group consisting of unsubstituted phenylene and phenylene containing substituent(s);

$L_7$, $L_8$, $L_9$ and $L_{10}$ are each independently anyone selected from the group consisting of unsubstituted phenyl and phenyl containing substituent(s);

at least one of $L_1$ and $L_2$ is phenylene containing substituent(s);

$L_3$, $L_4$, $L_5$, $L_6$, $L_7$, $L_8$, $L_9$ and $L_{10}$ are required to satisfy at least one of the following conditions:

(1) at least one of $L_3$, $L_4$, $L_5$ and $L_6$ is phenylene containing substituent(s);

(2) at least one of $L_7$, $L_8$, $L_9$ and $L_{10}$ is phenyl containing substituent(s).

The exemplary unsubstituted phenylene may be

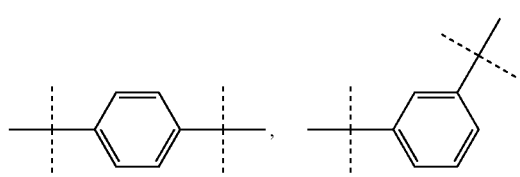

or

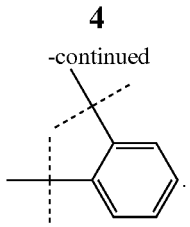

The exemplary substituted phenylene may be

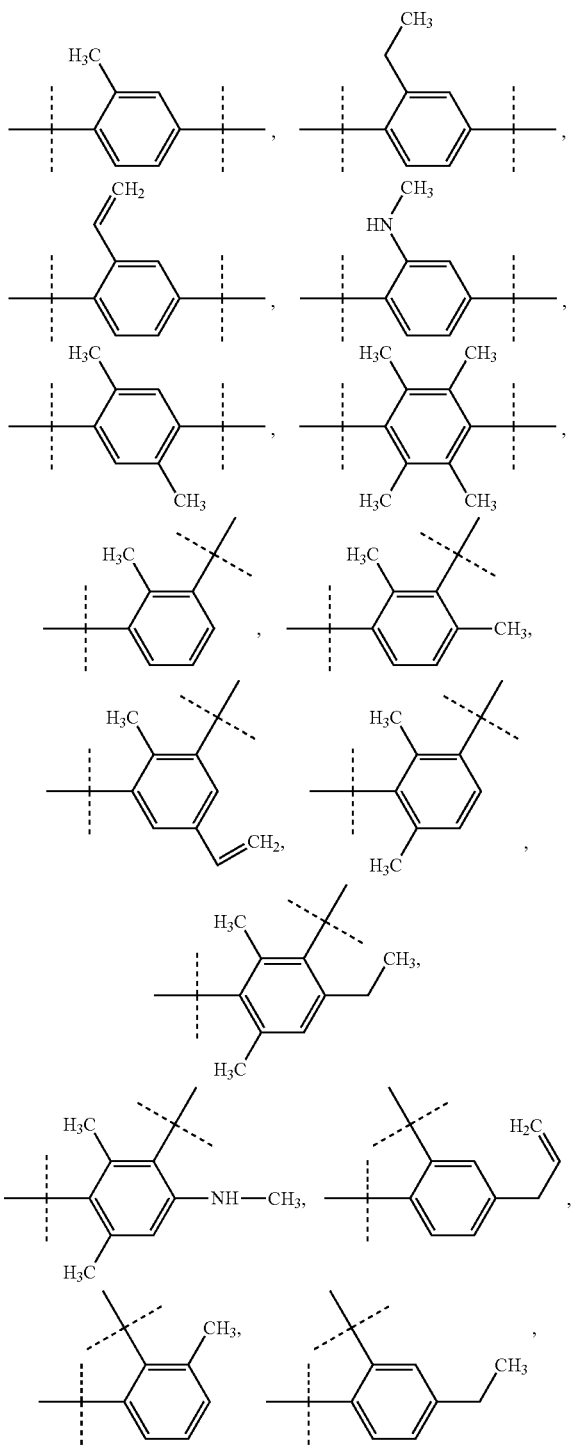

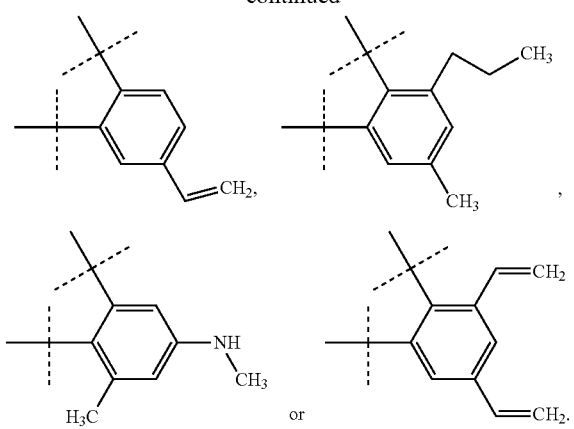

The phenyl containing substituent(s) may be

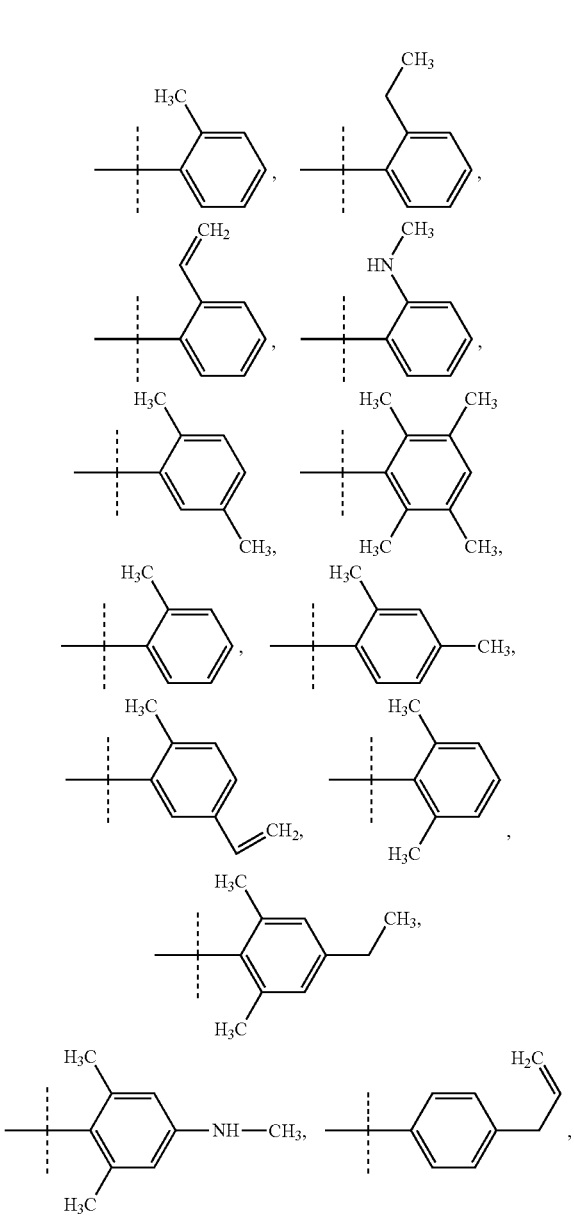

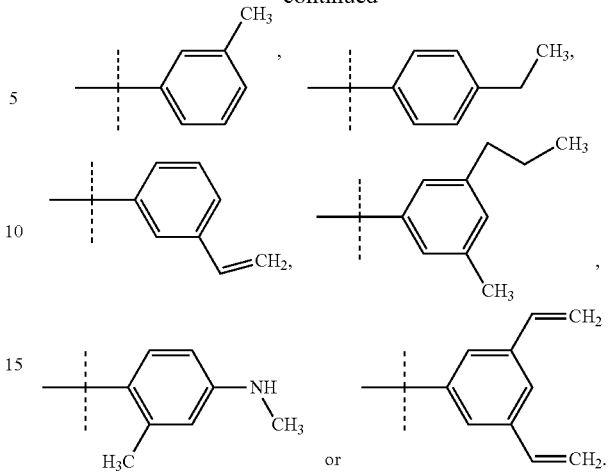

In one specific embodiment, $L_1$, $L_2$, $L_3$, $L_4$, $L_5$ and $L_6$ are each independently anyone selected from the group consisting of

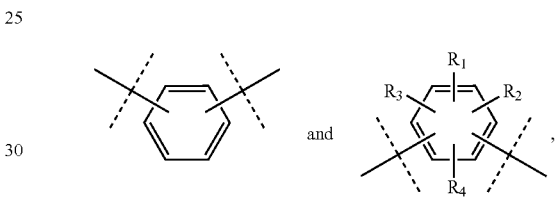

wherein $R_1$, $R_2$, $R_3$ and $R_4$ are each independently selected from the group consisting of hydrogen atom, deuterium atom, linear chain or branched chain alkyl group of C1-C5, and linear chain or branched chain alkoxy group of C1-C5.

In one specific embodiment, $L_7$, $L_8$, $L_9$ and $L_{10}$ are each independently anyone selected from the group consisting of

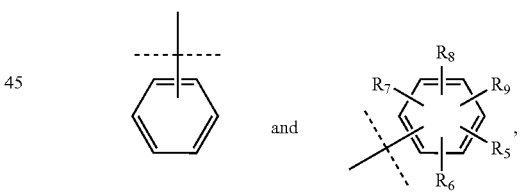

wherein $R_5$, $R_6$, $R_7$, $R_8$ and $R_9$ are each independently selected from the group consisting of hydrogen atom, deuterium atom, linear chain or branched chain alkyl group of C1-C5, and linear chain or branched chain alkoxy group of C1-C5.

Examples of the linear chain or branched chain alkyl group of C1-C5 include methyl, ethyl, n-propyl, n-butyl, t-butyl, pentyl and the like.

Examples of the linear chain or branched chain alkoxyl group of C1-C5 include methoxy, ethoxy, n-propoxy, t-butoxy and the like.

In one preferred specific embodiment, -$L_4$-$L_8$ and -$L_5$-$L_9$ are the same, and -$L_3$-$L_7$ and -$L_6$-$L_{10}$ are the same.

In one preferred specific embodiment, the hole transporting material is anyone selected from the group consisting of

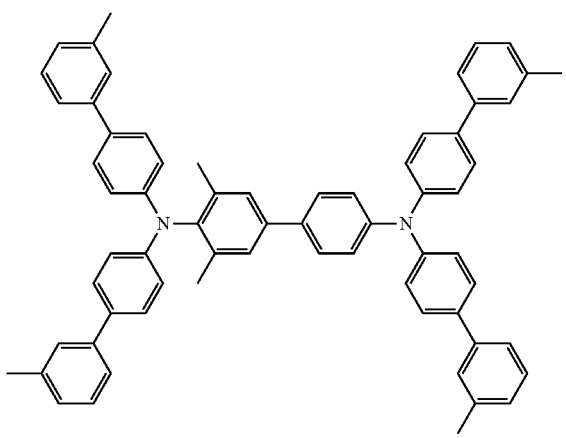

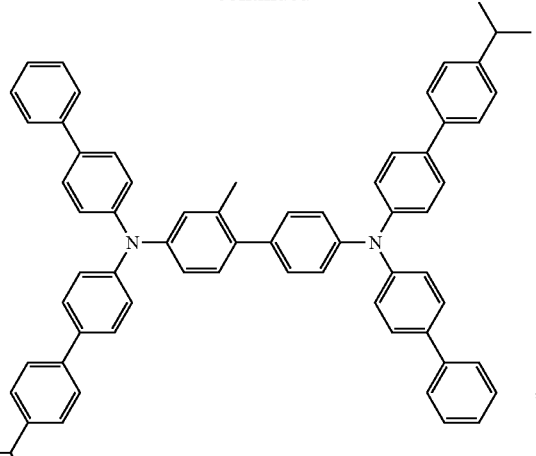

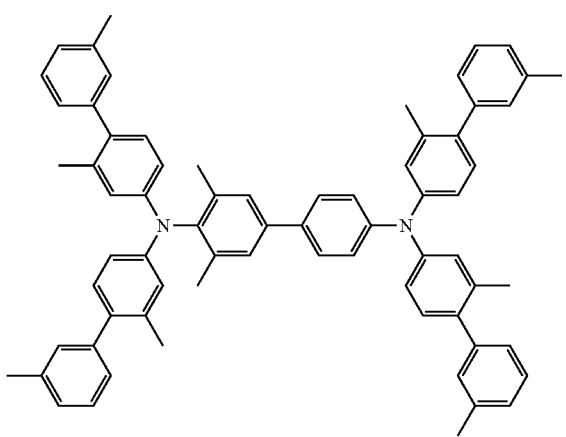

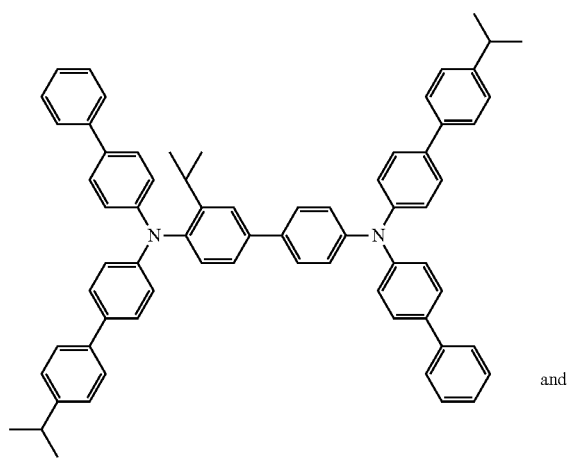

and

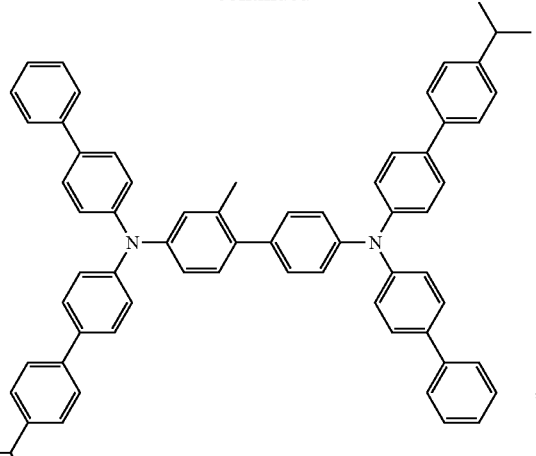

or a combination of at least two selected therefrom.

In one specific embodiment, the hole transporting material has a hole mobility rate of $9\times10^{-5}$–$5\times10^{-4}$ cm$^2$/V·S, e.g. $1.0\times10^{-4}$ cm$^2$/V·S, $2.0\times10^{-4}$ cm$^2$/V·S, $3.0\times10^{-4}$ cm$^2$/V·S, $4.0\times10^{-4}$ cm$^2$/V·S and the like, and a solubility in NMP of 10 g/L or more at 25° C., e.g. 11 g/L, 13 g/L, 15 g/L, 16 g/L, 19 g/L, 20 g/L and the like.

The mobility rate of $9\times10^{-5}$–$5\times10^{-4}$ cm$^2$/V·S can ensure no occurrence of crosstalk between pixels, and the solubility of 10 g/L or more in NMP can meet the MASK cleaning requirements.

In one specific embodiment, the present invention further provides a hole transporting layer comprising the hole transporting material as stated above.

Preferably, the hole transporting layer has a thickness of 600-2300 Å, e.g. 620 Å, 660 Å, 690 Å, 730 Å, 750 Å, 780 Å, 800 Å, 830 Å, 850 Å, 870 Å, 900 Å, 930 Å, 950 Å, 970 Å, 990 Å, 1020 Å, 1060 Å, 1090 Å, 1130 Å, 1150 Å, 1180 Å, 1200 Å, 1230 Å, 1250 Å, 1270 Å, 1300 Å, 1330 Å, 1350 Å, 1370 Å, 1390 Å, 1400 Å, 1430 Å, 1450 Å, 1470 Å, 1490 Å, 1500 Å, 1530 Å, 1650 Å, 1670 Å, 1790 Å, 1800 Å, 1930 Å, 1950 Å, 2070 Å, 2190 Å, 2200 Å, 2330 Å, 2450 Å, 2470 Å, 2490 Å and the like.

Preferably, the hole transporting layer is doped with a P-type organic material in the hole transporting material as stated above.

Preferably, the p-type organic material has a doping ratio of 1 to 10 wt % in the hole transporting layer, e.g. 2 wt %, 3 wt %, 4 wt %, 5 wt %, 6 wt %, 7 wt %, 8 wt %, 9 wt % and the like.

The present invention further provides an OLED display panel comprising a first electrode and a second electrode, wherein a laminate comprising a light emitting layer and a hole transporting layer is provided between the first electrode and the second electrode; the hole transporting layer comprises the hole transporting material above, or the hole transporting layer is the hole transporting layer above.

The exemplary material of the first electrode is anyone selected from the group consisting of indium tin oxide (ITO), indium zinc oxide (IZO) and tin dioxide, or a combination of at least two selected therefrom.

The exemplary material of the second electrode is anyone selected from the group consisting of magnesium, aluminum, silver, or a combination of at least two selected therefrom.

In one preferred specific embodiment, the laminate further comprises anyone of a hole injection layer, a hole transporting layer, an electron transporting layer, and an electron injection layer, or a combination of at least two selected therefrom.

The exemplary material of the hole injection layer is anyone selected from the group consisting of

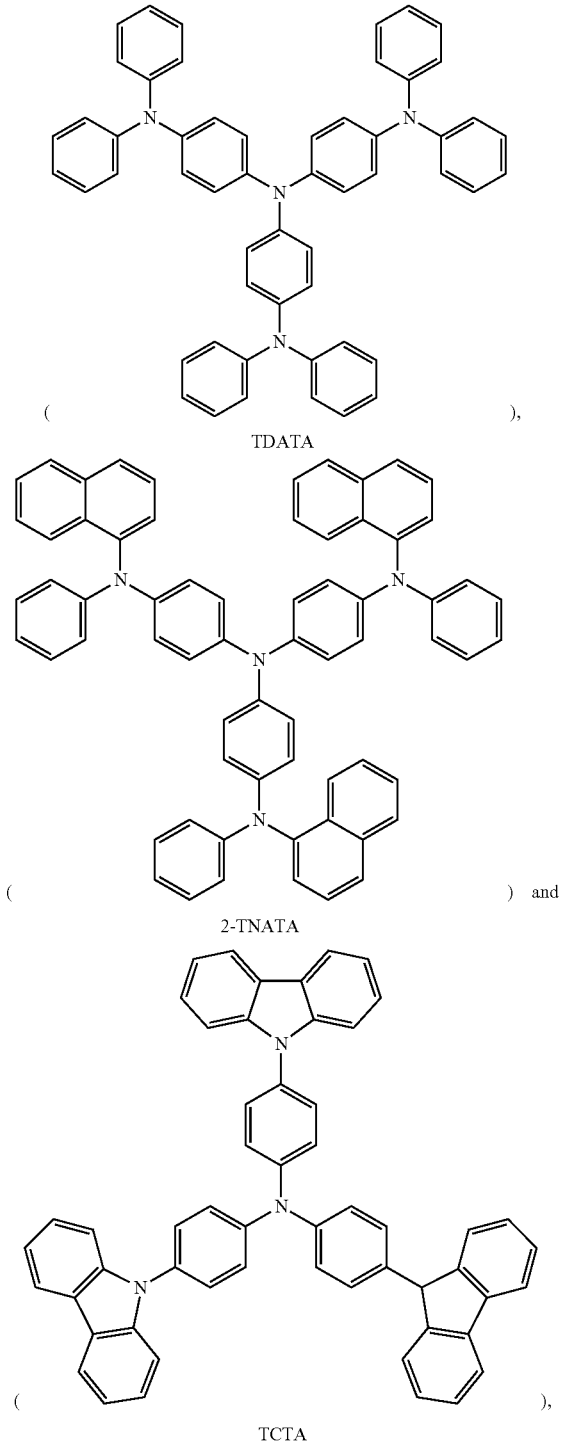

or a combination of at least two selected therefrom.

The exemplary material of the hole transporting layer is

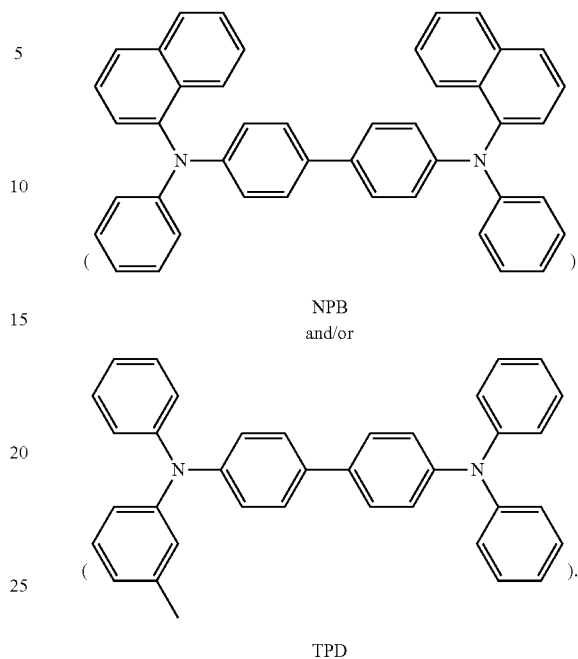

The exemplary material of the electron transporting layer is anyone selected from the group consisting of BPhen

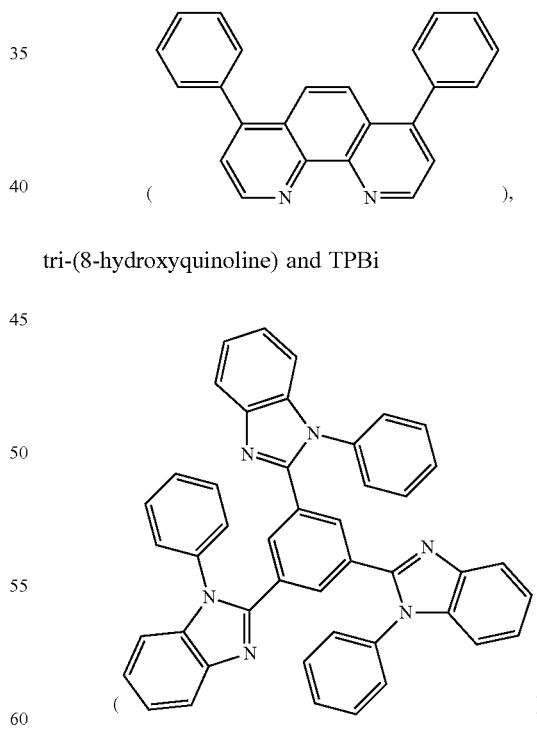

tri-(8-hydroxyquinoline) and TPBi or a combination of at least two selected therefrom.

In one specific embodiment, the light emitting layer comprises anyone selected from the group consisting of a blue light emitting unit, a green light emitting unit and a red light emitting unit, or a combination of at least two selected therefrom.

Preferably, the blue light emitting unit, the green light emitting unit and the red light emitting unit have common hole transporting layer comprising the hole transporting material above, or the common hole transporting layer is the hole transporting layer above.

Preferably, the common hole transporting layer has a thickness of 600-1500 Å, e.g. 620 Å, 660 Å, 690 Å, 730 Å, 750 Å, 780 Å, 800 Å, 830 Å, 850 Å, 870 Å, 900 Å, 930 Å, 950 Å, 970 Å, 990 Å, 1020 Å, 1060 Å, 1090 Å, 1130 Å, 1150 Å, 1180 Å, 1200 Å, 1230 Å, 1250 Å, 1270 Å, 1300 Å, 1330 Å, 1350 Å, 1370 Å, 1390 Å, 1400 Å, 1430 Å, 1450 Å, 1470 Å, 1490 Å and the like.

In one specific embodiment, the green light emitting unit and the red light emitting unit adopt a phosphorescent material; and the blue light emitting unit uses a fluorescent material.

In one specific embodiment, the OLED display panel has a red light external quantum efficiency of 16% or more, a green light external quantum efficiency of 16% or more, and a blue light external quantum efficiency of 10% or more.

In one specific embodiment, the laminate further comprises anyone selected from the group consisting of a hole injection layer, an electron transporting layer, and an electron injection layer, or a combination of at least two selected therefrom.

In one specific embodiment, the OLED display panel comprises in turn from bottom to top a first electrode, a hole injection layer, a hole transporting layer, a light emitting layer, an electron transporting layer, an electron injection layer, and a second electrode.

In one specific embodiment, the first electrode is an anode, and the second electrode is a cathode.

In one specific embodiment, the OLED display panel of the present invention illustratively has the structure shown in FIG. 1, including a substrate 101, a first electrode 102 disposed on the substrate 101, a hole transporting layer 103 and a light emitting layer 104 sequentially stacked on the first electrode 102, and a second electrode 105 formed thereon.

Figure 2:
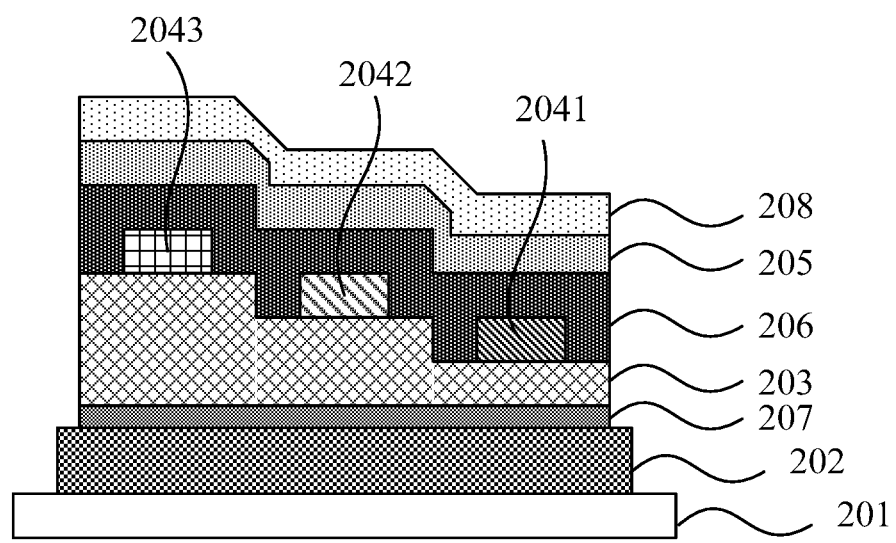
FIG. 2 shows a schematic cross-sectional structure view of another OLED display panel according to one specific embodiment of the present invention.

In another specific embodiment, the OLED display panel of the present invention illustratively has the structure of FIG. 2, including a substrate 201, a first electrode 202 disposed on the substrate 201, a buffer layer 207, a hole transporting layer 203 and an electron transporting layer 206 sequentially stacked on the first electrode 202, and a second electrode 205 formed thereon, and a cap layer 208 overlying the second electrode 205. On the hole transporting layer 203, there are also a blue light emitting unit 2041, a green light emitting unit 2042, and a red light emitting unit 2043, wherein the electron transporting layer 206 covers the blue light emitting unit 2041, the green light emitting unit 2042, and the red light emitting unit 2043, as well as the gaps between the blue light emitting unit 2041, the green light emitting unit 2042, and the red light emitting unit 2043.

Figure 3:
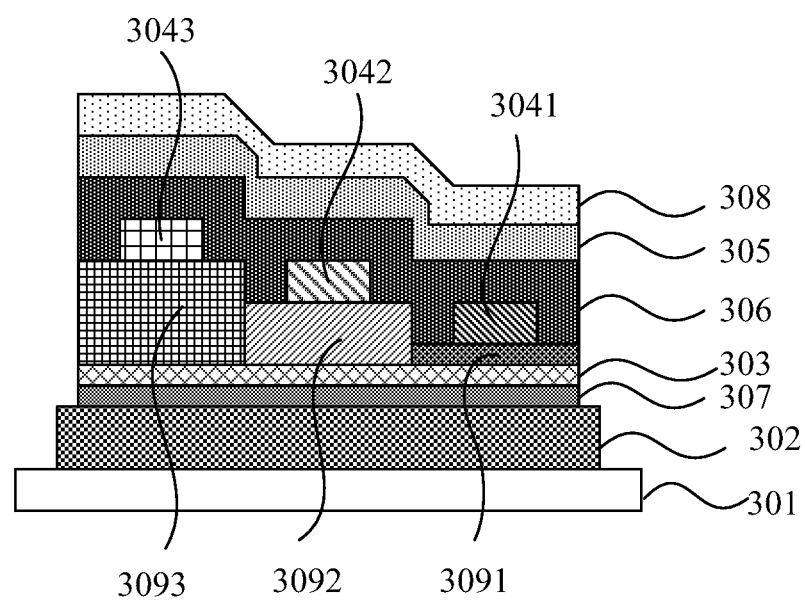
FIG. 3 shows a schematic cross-sectional structure view of yet another OLED display panel according to one specific embodiment of the present invention.

In yet another specific embodiment, the OLED display panel of the present invention illustratively has the structure of FIG. 3, including a substrate 301, a first electrode 302 disposed on the substrate 301, a buffer layer 307, a common hole transporting layer 303, an independent hole transporting layer (red light independent hole transporting layer 3093, green light independent hole transporting layer 3092, and blue light independent hole transporting layer 3091) and an electron transporting layer 306 sequentially stacked on the first electrode 302, and a second electrode 305 formed thereon, and a cap layer 308 overlying the second electrode 305. A red light emitting unit 3043 is provided on the red light independent hole transporting layer 3093 of the independent hole transporting layer; a green light emitting unit 3042 is provided on the green light independent hole transporting layer 3092 of the independent hole transporting layer; a blue light emitting unit 3041 is provided on the blue light independent hole transporting layer 3091 of the independent hole transporting layer. The electron transporting layer 306 covers the blue light emitting unit 3041, the green light emitting unit 3042, and the red light emitting unit 3043 and the gaps between the blue light emitting unit 3041, the green light emitting unit 3042, and the red light emitting unit 3043.

Those skilled in the art shall know that the OLED display panels listed in the present invention do not include all of the structures, and those skilled in the art can also design the display panel according to actual situations. For example, those skilled in the art can set up different thicknesses to the hole transporting layers corresponding to the red light emitting unit, the blue light emitting unit and the green light emitting unit, so as to satisfy the microcavity effect produced by the light emitting units of different colors. Those skilled in the art can also provide an exclusive transporting layer between the light emitting unit and the common hole transporting layer. For example, a red light-hole transporting unit is provided between the luminescent material of the red light emitting unit and the common hole transporting layer; a green light-hole transporting unit is provided between the luminescent material of the green light emitting unit and the common hole transporting layer; and a blue light-hole transporting unit is provided between the luminescent material of the blue light emitting unit and the common hole transporting layer.

The present invention further provides an electronic device comprising the OLED display panel above.

The compounds of the present invention having a structure represented by formula (I) can be synthesized by the prior art, for example:

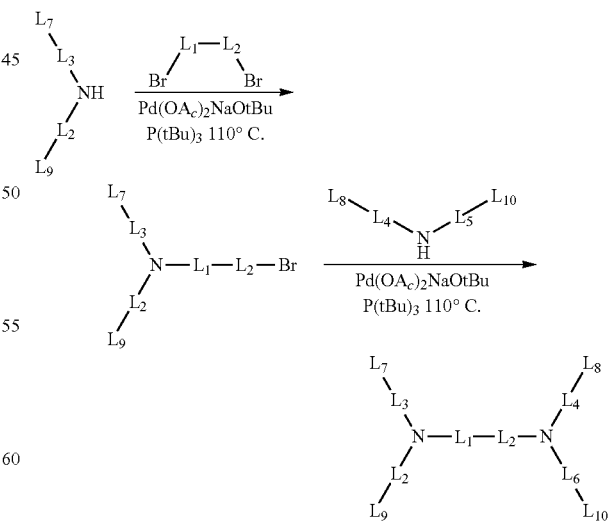

when -$L_4$-$L_8$ and -$L_5$-$L_9$ are the same, and -$L_3$-$L_7$ and -$L_6$-$L_{10}$ are the same, the preparation process can be simplified as:

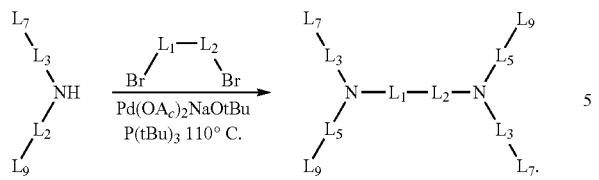

Synthesis Example 1

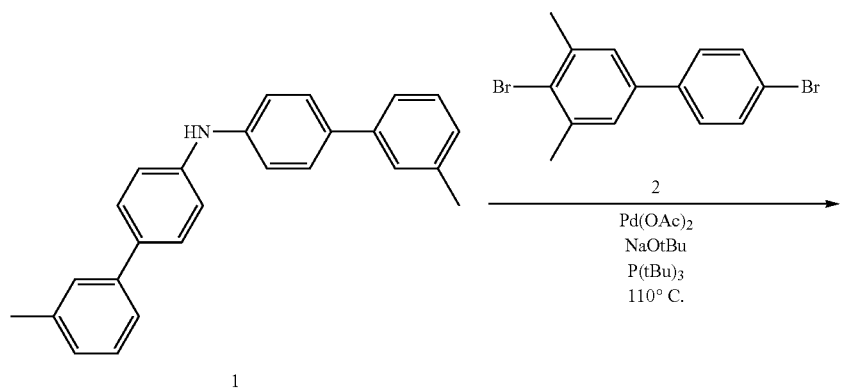

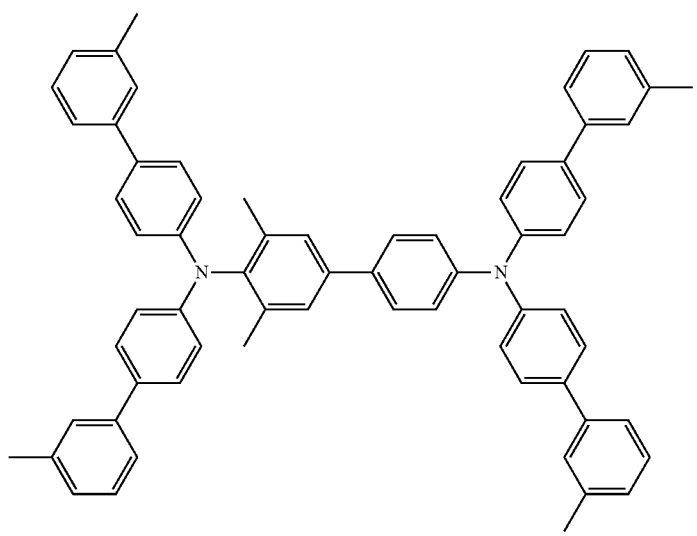

To a 500 mL three-necked flask were added 5 g (14.3 mmol) of an intermediate 1, 2.3 g (6.9 mmol) of an intermediate 2, 30.9 mg (0.138 mmol) of palladium acetate and 1.1 g (13.9 mmol) of sodium t-butoxide. The flask was filled with nitrogen; 100 mL of dehydrated toluene and 0.12 mL (0.276 mmol) of tri-tert-butylphosphine were added to the flask. The mixture was placed in an oil bath and slowly heated to 110° C. for 8 hours and allowed to stand overnight. The resulted solid was dissolved in dichloromethane, washed with 300 mL of saturated brine, and the organic layer was dried with magnesium sulfate. Recrystallization was made by using a mixed solvent of toluene and ethanol to give 4.5 g (5.17 mmol) of a target compound with a yield of 75%. Mass spectrometry M/Z=876.5 was obtained by LC-MS.

Synthesis Example 2

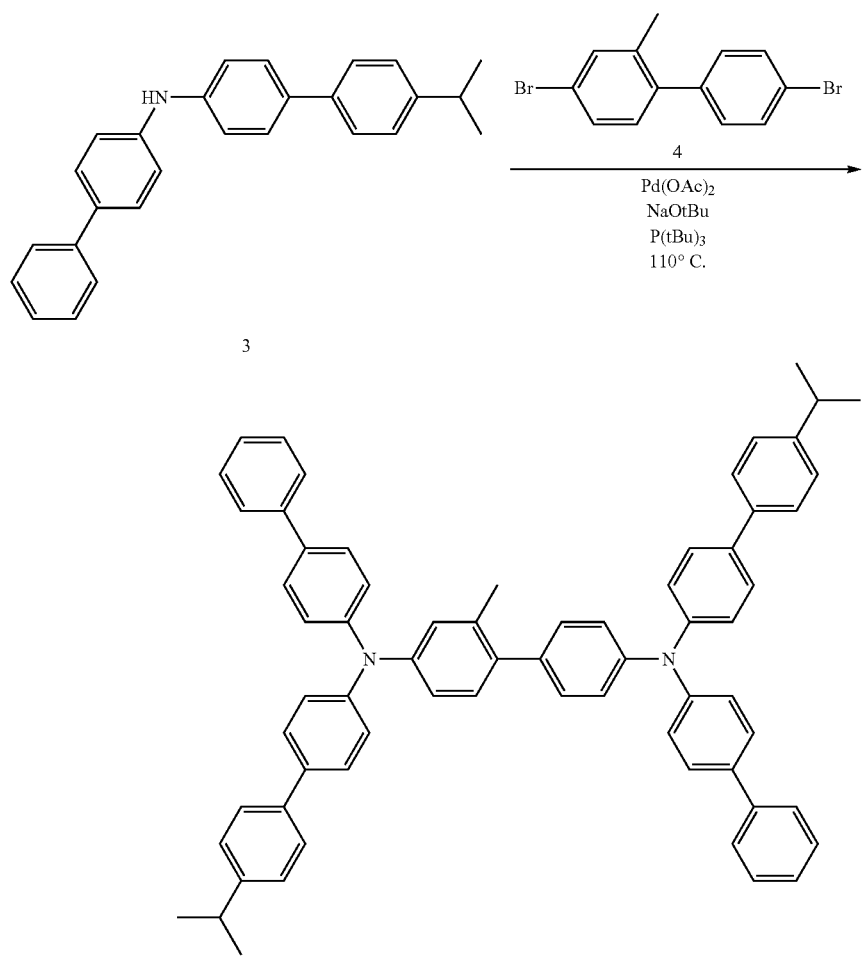

To a 500 mL three-necked flask were added 5 g (13.7 mmol) of an intermediate 3, 2.2 g (6.7 mmol) of an intermediate 4, 29.8 mg (0.134 mmol) of palladium acetate and 1.2 g (14.4 mmol) of sodium t-butoxide. The flask was filled with nitrogen; 100 mL of dehydrated toluene and 0.12 mL (0.268 mmol) of tri-tert-butylphosphine were added to the flask. The mixture was placed in an oil bath and slowly heated to 110° C. for 8 hours and allowed to stand overnight. The resulted solid was dissolved in dichloromethane, washed with 300 mL of saturated brine, and the organic layer was dried with magnesium sulfate. Recrystallization was made by using a mixed solvent of toluene and ethanol to give 4.1 g (4.69 mmol) of a target compound with a yield of 70%. Mass spectrometry M/Z=890.5 was obtained by LC-MS.

Example 1

An OLED display panel having the structure shown in FIG. 2 was prepared by the following process.

On the substrate 201 of glass material, a reflective silver anode of 100 nm was formed, and then an ITO film layer was deposited at a film thickness of 15 nm to obtain a first electrode 202 as an anode. Then a mixed material of

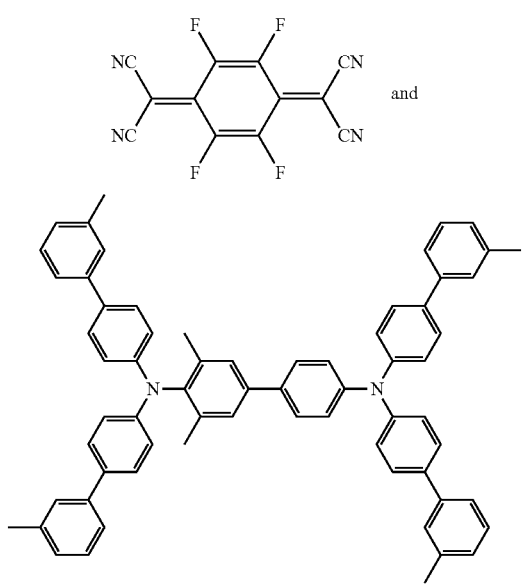

was evaporated as a buffer layer, wherein the mixing ratio was 5:95 (by weight). Thereafter,

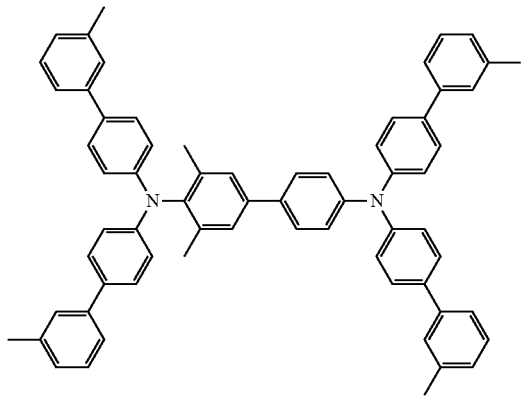

was vacuum-evaporated by using a fine metal mask to form films having thicknesses of 210 nm, 170 nm and 130 nm respectively on red light, green light and blue light pixels, so as to give a hole transporting layer 203 having a hole mobility rate of $2 \times 10^{-4}$ cm$^2$/V·S and a solubility in NMP of 15 g/L. 40 nm of

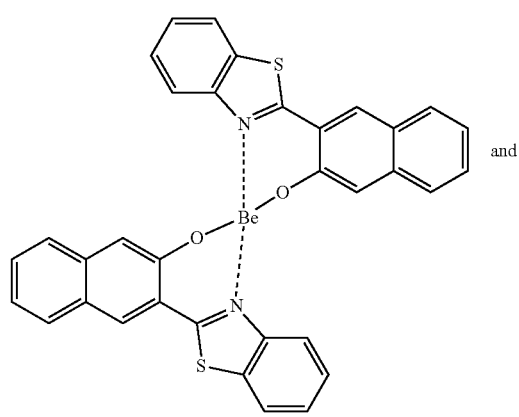

was evaporated at a ratio of 95:5 to form an emission red light emitting unit 2043; 40 nm of

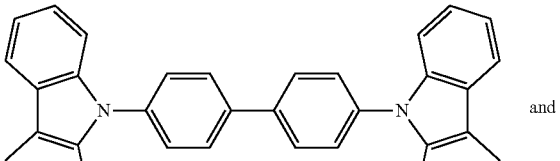

and

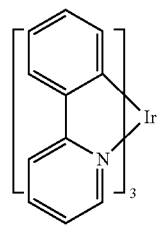

was evaporated at a ratio of 9:1 to form an emission green light emitting unit 2042; 30 nm of

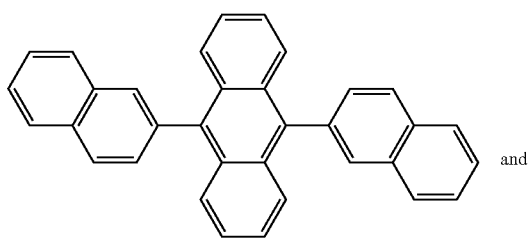

and

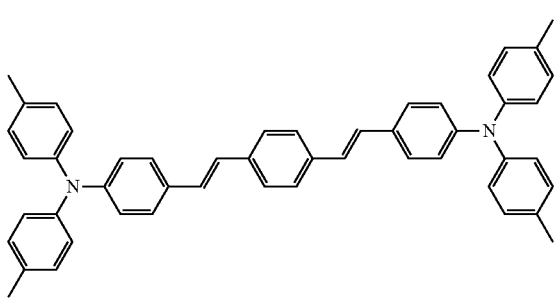

was evaporated at a ratio of 95:5 to form an emission blue light emitting unit 2041; an evaporation material of

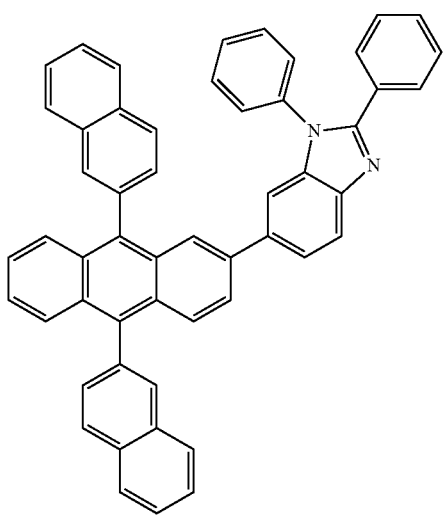

and

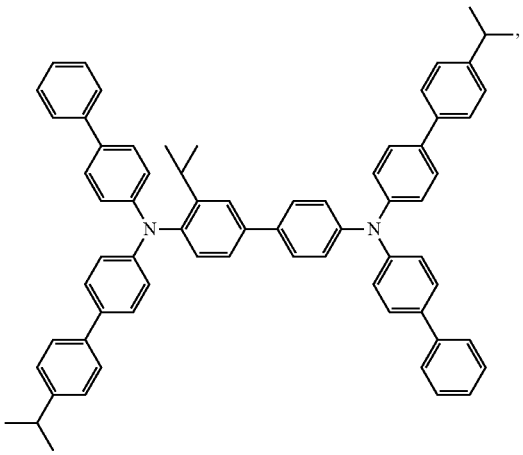

wherein the hole mobility rate was $2.5 \times 10^{-4}$ cm$^2$/V·S; and the solubility thereof in NMP was 12 g/L.

Example 4

It is different from Example 1 that the material of the hole transporting layer was replaced with

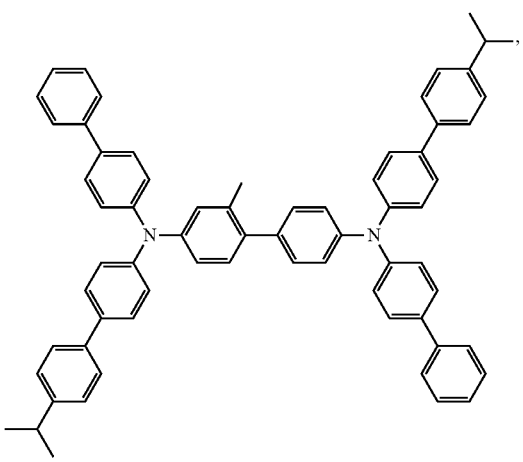

wherein the hole mobility rate was $2.4 \times 10^{-4}$ cm$^2$/V·S; and the solubility thereof in NMP was 12 g/L.

Comparison Example 1

It is different from Example 1 that the material of the hole transporting layer was replaced with was co-evaporated at a ratio of 1:1 to form an electron transporting layer 206 having a thickness of 30 nm, and then to form a magnesium-silver (having a mass ratio of 9:1) alloy having a thickness of 15 nm as a second electrode 205. 60 nm of a cap layer 8-hydroxyquinoline aluminum was evaporated, and then covered with protective glass sheets.

Example 2

It is different from Example 1 that the material of the hole transporting layer was replaced with

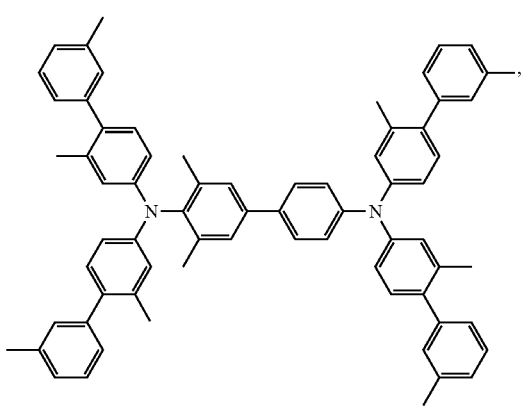

wherein the hole mobility rate was $1.2 \times 10^{-4}$ cm$^2$/V·S; and the solubility thereof in NMP was 25 g/L.

Example 3

It is different from Example 1 that the material of the hole transporting layer was replaced with

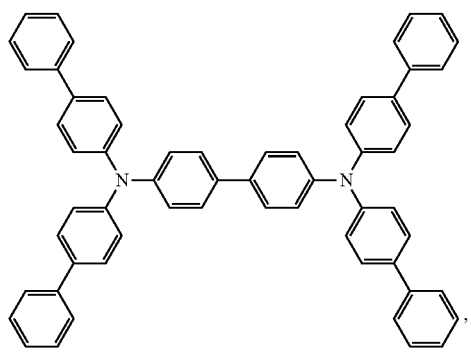 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

wherein the hole mobility rate was $3\times10^{-4}$ cm$^2$/V·S; and the solubility thereof in NMP was 1.2 g/L.

Comparison Example 2

It is different from Example 1 that the material of the hole transporting layer was replaced with

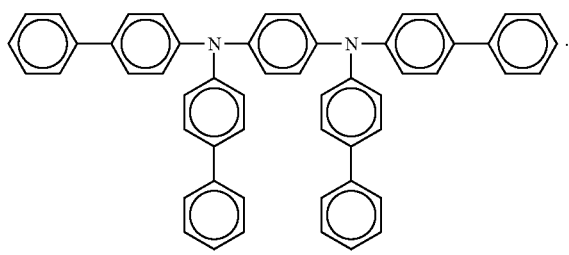

Performance Tests

Performance tests of the OLED display panels in the Examples and Comparison Examples were carried out.

(1) Device voltage test method: the program being transferred to the B screen, testing the voltage of the blue light at 10 mA/cm$^2$;

(2) Crosstalk test method: the program being transferred to the B screen in a dark room, testing the intensity ratio of the green light of adjacent pixels when the blue light intensity was 0.1 Cd/m$^2$, $L_{Green}/L_{Blue}$;

(3) Mask Cleaning Effect:

the time required for all the materials on the MASK of the red light of the hole transporting layer 203 to be completely cleaned at a fixed ultrasonic frequency of 40 kHz and at a temperature of 25° C.

Test results can be seen in Table 1.

TABLE 1

| | Device voltage | $L_{Green}/L_{Blue}$ | Mask cleaning time |
|---|---|---|---|
| Example 1 | 102% | 1.9% | 20 s |
| Example 2 | 108% | 2.1% | 15 s |
| Example 3 | 102% | 1.7% | 20 s |
| Example 4 | 102% | 1.7% | 20 s |
| Com. Example 1 | 100% | 1.5% | 80 s |
| Com. Example 2 | 103% | 1.7% | 65 s |

The applicant stated that the present invention illustrates the detailed process equipment and process flow by the above-described examples, but the present invention is not limited to the above-described detailed process equipment and process flow. That is, it does not mean that the present invention cannot be carried out unless the above-described detailed process equipment and process flow are used. Those skilled in the art shall know that improvements over the embodiments disclosed here, equivalent replacements of the raw materials of the present invention, addition of auxiliary ingredients, selection of specific means and the like can fall within the protection and disclosure scope of the present invention.

What is claimed is:

1. A hole transporting material, wherein the hole transporting material comprises any one of the following structure:

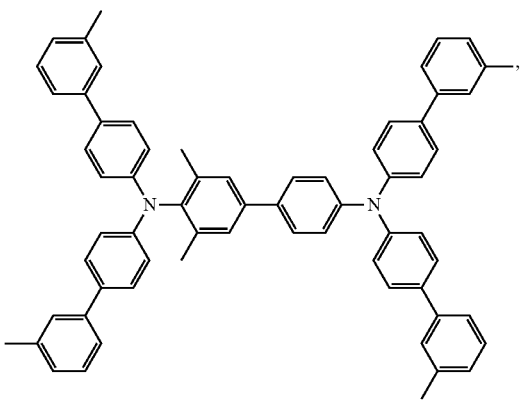

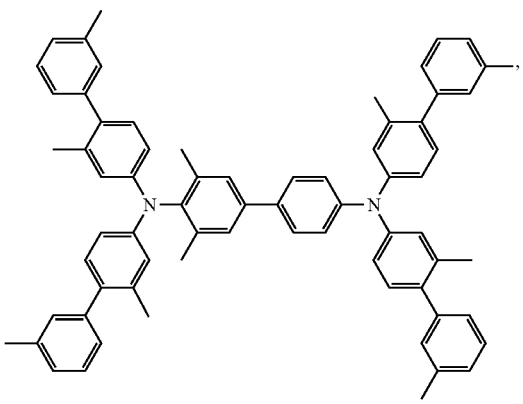

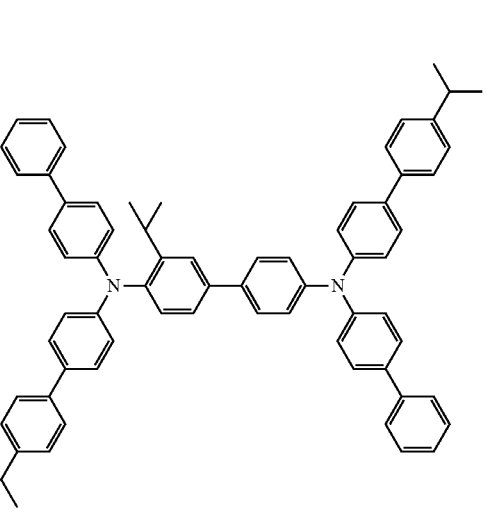

and

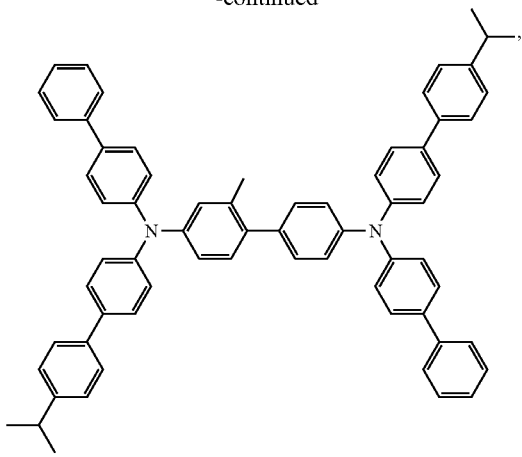

or a combination of at least two selected therefrom.

2. The hole transporting material claimed in claim 1, characterized in that the hole transporting material has a hole mobility rate of $9\times10^{-5}$–$5\times10^{-4}$ cm$^2$/V·S, and a solubility in NMP of 10 g/L or more at 25° C.

3. A hole transporting layer, characterized in that the hole transporting layer comprises the hole transporting material claimed in claim 1.

4. The hole transporting layer claimed in claim 3, characterized in that the hole transporting layer has a thickness of 600-2300 Å.

5. The hole transporting layer claimed in claim 3, characterized in that the hole transporting layer is doped with a P-type organic material in the hole transporting material.

6. The hole transporting layer claimed in claim 5, characterized in that the p-type organic material has a doping ratio of 1 to 10 wt % in the hole transporting layer.

7. An OLED display panel, characterized in that the OLED display panel comprises a first electrode and a second electrode, wherein a laminate comprising a light emitting layer and a hole transporting layer is provided between the first electrode and the second electrode; and the hole transporting layer comprises the hole transporting material claimed in claim 1, or the hole transporting layer is the hole transporting layer claimed in claim 3.

8. The OLED display panel claimed in claim 7, characterized in that the light emitting layer comprises anyone selected from the group consisting of a blue light emitting unit, a green light emitting unit and a red light emitting unit, or a combination of at least two selected therefrom.

9. The OLED display panel claimed in claim 8, characterized in that the green light emitting unit and the red light emitting unit adopt a phosphorescent material; and the blue light emitting unit uses a fluorescent material.

10. The OLED display panel claimed in claim 8, characterized in that the OLED display panel has a red light external quantum efficiency of 16% or more, a green light external quantum efficiency of 16% or more, and a blue light external quantum efficiency of 10% or more.

11. The OLED display panel claimed in claim 7, characterized in that a blue light emitting unit, a green light emitting unit and a red light emitting unit have common hole transporting layer comprising the hole transporting material claimed in claim 1.

12. The OLED display panel claimed in claim 11, characterized in that the common hole transporting layer has a thickness of 600-1500 Å.

13. The OLED display panel claimed in claim 7, characterized in that the laminate further comprises at least one of a hole injection layer, an electron transporting layer, and an electron injection layer.

14. The OLED display panel claimed in claim 7, characterized in that the OLED display panel comprises in turn from bottom to top a first electrode, a hole injection layer, a hole transporting layer, a light emitting layer, an electron transporting layer, an electron injection layer, and a second electrode.

15. The OLED display panel claimed in claim 7, characterized in that the first electrode is an anode, and the second electrode is a cathode.

16. The OLED display panel claimed in claim 7, characterized in that a blue light emitting unit, a green light emitting unit and a red light emitting unit have common hole transporting layer which is the hole transporting layer claimed in claim 3.

\* \* \* \* \*